United States Patent
Suzuki et al.

(10) Patent No.: US 10,047,338 B2
(45) Date of Patent: Aug. 14, 2018

(54) ALGAE CULTIVATION METHOD AND PRODUCTION METHOD FOR OSMOTIC PRESSURE REGULATOR

(71) Applicants: euglena Co., Ltd., Tokyo (JP); SHIMIZU CORPORATION, Tokyo (JP)

(72) Inventors: Kengo Suzuki, Yokohama (JP); Ryohei Nakano, Yokohama (JP); Hideyuki Adachi, Yokohama (JP); Ayaka Nakashima, Yokohama (JP); Eriko Yoshida, Yokohama (JP); Masaharu Tasaki, Tokyo (JP); Yoichi Kuroiwa, Tokyo (JP); Keisuke Kojima, Tokyo (JP); Takeshi Hasegawa, Kashiwa (JP)

(73) Assignees: EUGLENA CO., LTD., Minato-ku, Tokyo (JP); SHIMIZU CORPORATION, Chuo-ku, Tokyo (JP)

( * ) Notice: Subject to any disclaimer, the term of this patent is extended or adjusted under 35 U.S.C. 154(b) by 0 days.

(21) Appl. No.: 15/304,601

(22) PCT Filed: Apr. 16, 2015

(86) PCT No.: PCT/JP2015/061747
§ 371 (c)(1),
(2) Date: Oct. 17, 2016

(87) PCT Pub. No.: WO2015/159959
PCT Pub. Date: Oct. 22, 2015

(65) Prior Publication Data
US 2017/0037360 A1    Feb. 9, 2017

(30) Foreign Application Priority Data

Apr. 17, 2014 (JP) ................... 2014-085444
Apr. 17, 2014 (JP) ................... 2014-085587

(51) Int. Cl.
*C12P 13/04* (2006.01)
*C12N 1/12* (2006.01)
(Continued)

(52) U.S. Cl.
CPC ................. *C12N 1/12* (2013.01); *C12N 1/20* (2013.01); *C12P 13/001* (2013.01); *C12P 13/04* (2013.01); *C12P 19/44* (2013.01)

(58) Field of Classification Search
CPC ...................................................... C12P 13/04
See application file for complete search history.

(56) References Cited

U.S. PATENT DOCUMENTS

2009/0181434 A1   7/2009  Aikens et al.
2012/0301563 A1   11/2012 Aikens et al.
(Continued)

FOREIGN PATENT DOCUMENTS

JP    6-107611 A    4/1994
JP    8-56648 A    3/1996
(Continued)

OTHER PUBLICATIONS

JP 06-239814 A, KK Kaiyo Bio Technol Kenkyusho, English machine translation of specification.*
(Continued)

*Primary Examiner* — Rosanne Kosson
(74) *Attorney, Agent, or Firm* — Sughrue Mion, PLLC

(57) ABSTRACT

An algae culture method capable of efficiently producing an osmotic pressure adjusting substance, a production method of the substance, and an algae culture method for recovering carbon dioxide from a mixed gas containing carbon dioxide and sulfurous acid gas. The methods involve preparing a plurality of enrichment cultures each containing betaine by culturing a culture of microalgae derived from an environmental specimen under a photoautotrophic condition and
(Continued)

under a plurality of culture conditions; making a cultivation plan in which an optimum enrichment culture suitable for a main culture is selected from the plurality of enrichment cultures; producing a main culture that contains betaine under the photoautotrophic condition and a salt concentration of 10 wt. % or more; and separating betaine. In the main culture, the algae containing betaine are cultured while the mixed gas containing sulfurous acid gas and carbon dioxide is blown to a culture solution of the algae.

14 Claims, 5 Drawing Sheets

(51) Int. Cl.
  *C12N 1/20* (2006.01)
  *C12P 19/44* (2006.01)
  *C12P 13/00* (2006.01)

(56) References Cited

U.S. PATENT DOCUMENTS

| | | |
|---|---|---|
| 2013/0115660 A1 | 5/2013 | Aikens et al. |
| 2013/0115689 A1 | 5/2013 | Aikens et al. |
| 2013/0115701 A1 | 5/2013 | Aikens et al. |
| 2013/0115702 A1 | 5/2013 | Aikens et al. |
| 2014/0051131 A1 | 2/2014 | Dodd et al. |
| 2014/0242688 A1 | 8/2014 | Aikens et al. |

FOREIGN PATENT DOCUMENTS

| | | |
|---|---|---|
| JP | 3459275 B2 | 10/2003 |
| JP | 2011-509085 A | 3/2011 |
| JP | 2015-101549 A | 6/2015 |
| WO | 2012/101459 A2 | 8/2012 |

OTHER PUBLICATIONS

JP 06-239814 A, KK Kaiyo Bio Technol Kenkyusho, English abstract.*
Tasaki et al., "Isolation and identification of thermophilic & halophilism microalgae in the Sultanate of Oman", Abstracts of the Annual Meeting of the Society for Biotechnology, Japan, Sep. 25, 2012, (Sep. 25, 2012), vol. 64, 4Gp09, p. 225 (total 3 pages).
Kuroiwa et al., "Classification of Halotolerance Cyanobacteria with Tightly Coiled Trichomes", Abstracts of the Annual Meeting of the Society for Biotechnology, Japan, Aug. 25, 2013 (Aug. 25, 2013), vol. 65, 2P-013, p. 107 (total 3 pages).
Cohen et al., "Adaptation to Hydrogen Sulfide of Oxygenic and Anoxygenic Photosynthesis among Cyanobacteria", Applied and Environmental Microbiology, Feb. 1986, vol. 51, No. 2, pp. 398-407.
Morita et al., "Microbial $CO_2$ fixation 10.—Evaluation of heat balance in cone-shaped helical tubular photobioreactor", CRIEPI Research Report, May 2000, U99054, pp. 1-28 (total 36 pages).
Kuroiwa et al., "Identification and physiological study of a newly halophilic algae *Spirulina subsalsa* var. *salina*, var. nov.", Abstracts of the Annual Meeting of the Society for Biotechnology, Japan, Aug. 5, 2014 (Aug. 5, 2014), vol. 66, 2P-011, p. 109 (total 3 pages).
International Search Report dated Jul. 21, 2015, issued by the International Searching Authority in application No. PCT/JP2015/061747.
Written Opinion of the International Searching Authority dated Jul. 21, 2015, issued by the International Searching Authority in application No. PCT/JP2015/061747.
Notification of Reasons for Refusal, dated Apr. 24, 2018, issued by the Japanese Patent Office in counterpart Japanese Patent Application No. 2014-085587.
Mackay, M., et al., "Organic Osmoregulatory Solutes in Cyanobacteria", Journal of General Microbiology, vol. 130, 1984, pp. 2177-2191.

* cited by examiner

1 : ENRICHMENT CULTURE PREPARATION
    PREPARATION STEP
2 : CULTIVATION PLAN STEP
3 : MAIN CULTIVATION STEP
    (INCLUDING: STEP OF SEPARATING
    AND OBTAINING OSMOTIC PRESSURE
    ADJUSTING SUBSTANCE)

4 : BETAINE
5 : GLUCOSYL GLYCEROL
6 : SODIUM CHLORIDE

ALGAE CULTIVATION METHOD AND PRODUCTION METHOD FOR OSMOTIC PRESSURE REGULATOR

CROSS-REFERENCE TO RELATED APPLICATIONS

This application is a 371 National Stage entry of PCT Application No. PCT/JP2015/061747 filed Apr. 16, 2015; which claims priority from Japanese Application No. 2014-085444, filed Apr. 17, 2014; and Japanese Application No. 2014-085587, filed Apr. 17, 2014. The entire disclosures of the each of the prior listed applications are hereby incorporated by reference.

TECHNICAL FIELD

The present invention relates to an algae culture method for culturing algae that contain a high concentration of an osmotic pressure adjusting substance such as betaine, and a production method of the substance. Further, the present invention relates to an algae culture method in which carbon dioxide is absorbed from a mixed gas containing sulfurous acid gas and carbon dioxide by culturing algae that contain betaine.

BACKGROUND ART

Betaine is conventionally used for a humectant of cosmetics, a seasoning, a flavor-improving agent, and the like. Betaine has been industrially produced at a certain level, where betaine is recovered from beet molasses, a by-product generated with the production of beet sugar (sucrose), mainly by using a chemical method, a method using an ion exchange resin, and the like (e.g., PATENT LITERATURE 1).

In recent years, new effectiveness of betaine has been recognized in pharmacological activities, such as improvement of a liver disease and a heart disease and a muscle strengthening effect, and as dairy feed and aquaculture feed. Thus, the demand of betaine is expected to increase in the future.

However, betaine is so far produced on a scale relying on secondary use of the by-product in sucrose production and a method for intentionally producing betaine as a primary product is not available. Thus, actions for meeting such increasing demand are needed.

Moreover, particularly now, as a greater focus is placed on the global warming issue, controlling emission quantity of carbon dioxide gas, which is one of green house gases, and reducing a carbon dioxide concentration in the atmosphere by fixing carbon dioxide become major issues. Under such circumstances, fuel resources other than fossil fuels are needed, and there are growing expectations for developing biofuels using higher plants and microalgae as raw materials. It is known that productivity of organic materials per unit area of microalgae are 10 times or more higher than oil palm, which belongs to higher plants and whose productivity is considered relatively high. Thus, expectations are further growing for microalgae.

On the other hand, in constructing a large-scale process to recover carbon dioxide and produce organic materials using the microalgae, there are many cases where an exhaust gas from a thermal power plant and the like is expected to be a source of carbon dioxide. However, there is a problem in that the exhaust gas contains sulfurous acid gas that is harmful to plants and microalgae. For example, based on an environmental annual report created by a domestic coal-fired power station, it is estimated that an exhaust gas that is released to the atmosphere after desulfurization and denitration treatments still contains sulfurous acid gas of about 150 ppm on average and carbon dioxide of 3 to 15 vol. %.

After diluting the exhaust gas approximately 6 to 30 times with an air or the like to adjust the concentration of carbon dioxide (about 0.5 vol. %) so as to be suitable for blowing to a culture solution of microalgae, the exhaust gas still contains sulfurous acid gas having a relatively high concentration of 5 to 25 ppm. Sulfurous acid gas of this concentration is still harmful for the conventional microalgae to be used in the production of organic materials such as biofuels.

According to known knowledge, only red algae *Galdieria* disclosed in PATENT LITERATURE 2 is known to be resistant to sulfurous acid gas. On the other hand, a recent market request for algal biomass production becomes increasingly larger for various applications, such as bio-diesel fuel, hydrocarbon fuel, hydrogen gas/alcohol fuel, a raw material of chemicals, a raw material of healthy and functional food, and a raw material of medicines.

In other words, in the present situation, culturing the microalgae are required to provide, additionally to absorbing carbon dioxide, consistent business potential including the use and sale of biomass resulting from the absorption of carbon dioxide. In order to meet such various applications, it is desirable to find a number of sulfur dioxide gas-resistant algae other than the red algae *Galdieria* and respond to the various applications requested by the market based on the diversity of the algae.

CITATION LIST

Patent Literature

PATENT LITERATURE 1: JP 6-107611 A
PATENT LITERATURE 2: Japanese Patent No. 3459275

SUMMARY OF INVENTION

Technical Problem

To solve such problems, the inventors searched for a new material that contains a high concentration of betaine and found that microalgae growing in a high salt environment accumulate betaine nearly 150 times higher than a conventional material. Accordingly, the inventors conducted intensive research and development on a raw material production method and the like using the microalgae.

As a result, the inventors completed the present invention by providing an algae culture method capable of efficiently producing an osmotic pressure adjusting substance such as betaine and a production method of the substance, the methods being performed by a simple process.

Further, the present invention has been made in the light of above circumstances and provides an algae culture method capable of recovering carbon dioxide from a mixed gas containing carbon dioxide and sulfurous acid gas.

Solution to Problem

To solve the above problems, the present invention is summarized in the following (1) to (6) and (14).

(1) An algae culture method, comprising:
an enrichment culture preparation step for preparing a plurality of enrichment cultures each including microalgae that contain betaine or glucosyl glycerol in an amount of 1 wt. % or more on a dry weight basis and having a different dominant species in microalgae flora by culturing an environmental specimen or a culture of microalgae derived from the environmental specimen under a photoautotrophic condition using a plurality of different culture conditions that include at least one of a temperature condition, a pH condition, and a salt concentration condition in which a final salt concentration in a culture is adjusted to 10 wt. % or more and 30 wt. % or less;

a step of making cultivation plan in which an optimum enrichment culture is selected from the plurality of enrichment cultures responding to an estimated temperature change and pH change caused in a medium during a main culture, and a series of culturing operations during the main cultivation are planned; and a main cultivation step for further producing a main culture that contains the microalgae containing the betaine or the glucosyl glycerol in an amount of 1 wt. % or more on a dry weight basis by performing the main culture under the photoautotrophic condition and the salt concentration condition of 10 wt. % or more based on the cultivation plan.

(2) The algae culture method according to (1), wherein the betaine or the glucosyl glycerol is separated and obtained from the main culture simultaneously with and/or after the main cultivation step.

(3) The algae culture method according to (1), wherein, in the main cultivation step, the main culture is performed under the salt concentration condition of 10 wt. % or more and 30 wt. % or less and a temperature condition of 30° C. or higher and lower than 50° C.

(4) The algae culture method according to (1), wherein, in the enrichment culture preparation step, the environmental specimen is collected from a natural environment where the microalgae inhabit and is cultured.

(5) The algae culture method according to (1), wherein the main cultivation step includes an enrichment culture changing step for selecting, from the plurality of enrichment cultures, the enrichment culture capable of growing at a present culture temperature and at pH4 or lower to avoid a decrease in the cell number of the microalgae due to predation by a predatory organism, and performing the main culture using the selected enrichment culture under the selected pH condition.

(6) The algae culture method according to (5), wherein the main cultivation step is performed throughout a year and the enrichment culture changing step is performed depending on a yearly temperature change.

(14) A production method of betaine or glucosyl glycerol, comprising:

an enrichment culture preparation step for preparing a plurality of enrichment cultures each including microalgae that contain betaine or glucosyl glycerol in an amount of 1 wt. % or more on a dry weight basis and having a different dominant species in microalgae flora by culturing an environmental specimen containing the microalgae or a culture of the microalgae derived from the environmental specimen under a photoautotrophic condition using a plurality of different culture conditions that include at least one of a temperature condition, a pH condition, and a salt concentration condition in which a final salt concentration in a culture is adjusted to 10 wt. % or more and 30 wt. % or less;

a step of making cultivation plan in which an optimum enrichment culture is selected from the plurality of enrichment cultures responding to an estimated temperature change and pH change caused in a medium during a main culture, and a series of culturing operations during the main cultivation are planned;

a main cultivation step for further producing a main culture that contains the microalgae containing the betaine or the glucosyl glycerol in an amount of 1 wt. % or more on a dry weight basis by performing the main culture under the photoautotrophic condition and the salt concentration condition of 10 wt. % or more based on the cultivation plan; and a step for separating and obtaining the betaine or the glucosyl glycerol from the main culture simultaneously with and/or after the main cultivation step.

Further, the present invention also provides the following means (7) to (13) in order to solve the above problems.

(7) The algae culture method according to (1), wherein, in the main cultivation step, the microalgae containing the betaine in an amount of 1 wt. % or more on a dry weight basis of the algae bodies is cultured while blowing a mixed gas containing sulfurous acid gas and carbon dioxide to a culture solution of the microalgae.

(8) The algae culture method according to the (7), wherein the microalgae are resistant to hydrogen sulfide gas.

(9) The algae culture method according to the (7), wherein the microalgae are resistant to sulfurous acid gas.

(10) The algae culture method according to the (7), wherein a salt concentration in the culture solution is 3 to 30 wt. %.

(11) The algae culture method according to the (7), wherein a concentration of sulfurous acid gas in the mixed gas is more than 5 ppm.

(12) The algae culture method according to the (7), wherein the mixed gas is generated by burning a sulfur-containing substance.

(13) The algae culture method according to the (7), wherein the microalgae are an enrichment culture obtained by inoculating water or soil collected from the natural environment where the microalgae inhabit into the culture solution and selecting microalgae which succeeded in growing in the culture.

Effects of Invention

In the present invention, the enrichment culture preparation step, the cultivation plan step, and the main cultivation step are carried out. This makes it possible to select an optimum enrichment culture from a variety of stocks consisting of the plurality of enrichment cultures prepared in the enrichment culture preparation step responding to the estimated temperature change and pH change caused during the main cultivation step, and plan the multicultural main culture having higher certainty and stability.

As a result, unlike a conventional commercial production technique for microalgae that is primarily carried out as a monoculture where a single species is cultured with a limited growth temperature condition, the present invention makes it possible to stably produce microalgae throughout the year by suppressing seasonal variation in productivity. By selectively using the enrichment cultures having different dominant species responding to an environmental temperature in each season, for example, using Pedinophyceae algae in winter and blue-green algae in summer, the culture can be performed throughout the year.

Further, usually the microalgae are continuously cultured primarily as a monoculture. Thus, when the culture solution is reused over a long period, the growth of the desired microalgae is sometimes inhibited by the presence of an autoinhibitor and its productivity decreases. In contrast, in the present invention, the microalgae can be stably produced throughout the year by selecting the optimum enrichment culture responding to the temperature change and pH change caused during the culturing time and appropriately switching microalgae species to be cultured, thereby circumventing, to no small extent, the growth inhibition by the autoinhibitor and the like caused by continuously culturing a single enrichment culture.

Further, in the present invention, the microalgae are cultured under the photoautotrophic condition in the enrichment culture preparation step and the main cultivation step. Thus, betaine or glucosyl glycerol as a useful substance is produced as a converted product of carbon dioxide while carbon dioxide is incorporated by photosynthesis. As a result, the present invention can contribute to suppressing the global warming caused by green house gases to some extent.

It is noted that, in the enrichment culture preparation step, the liquid or the soil collected from the natural environment where the microalgae inhabit may be cultured. A wide variety of enrichment cultures can be prepared while suppressing contamination by performing simple steps in which the liquid or the soil is added to a medium and the temperature and the salt concentration are kept at constant values.

It is noted that, in the present invention, the final salt concentrations in both the enrichment culture and the main culture are adjusted to 10 wt. % or more and 30 wt. % or less, thus the enrichment cultures in the both cultures are limited to microorganisms resistant to a high-salt concentration. Thus, the culture can be performed while taking a precautionary measure on an effect of the contamination, by which the growth of organisms other than halophilic microorganisms, for example, contaminated protozoa that prey on the microalgae containing betaine or glucosyl glycerol and other algae is suppressed, and the productivity of the desired microalgae are secured.

Further, when the above precautionary measure cannot prevent the contamination and the growth of the predatory organisms is observed or expected, in order to avoid the effect of the contamination, an enrichment culture capable of growing at the present culture temperature and at about pH4 or lower is newly selected from the plurality of enrichment cultures. The selected enrichment culture is then grown in the main culture under the same pH condition, so that the predatory organisms and the like can be easily exterminated while the productivity of betaine and the like is being secured.

As described above, in the microalgae culture method according to the present invention, the condition can be set so as to meet requirement for performing the precautionary measure and the effective extermination method against the contamination of the predatory organisms and other microorganisms, and such a setting allows the stable production of betaine and the like for a long period.

Further, according to the present invention, by using the microalgae of the present embodiment having a synthesis ability of betaine and the like, carbon dioxide can be incorporated by a simple process involving photosynthesis and the incorporated carbon dioxide can be converted to betaine and the like, a useful substance usable in many industries, such as a food industry, a pharmaceutical industry, and a feed industry.

Further, certain microalgae accumulate betaine in the algae bodies. It has been previously known that accumulation of betaine is involved in an osmotic pressure adjustment in the algae bodies. The present inventors have found that accumulation of betaine is deeply involved in sulfurous acid gas resistance and hydrogen sulfide gas resistance.

In the algae culture method according to the present invention, which has been completed based on the above finding, the algae can be cultured using a gas containing sulfurous acid gas and carbon dioxide, for example, an exhaust gas discharged from a thermal power plant and the like, as a source of carbon dioxide. As a result, the present invention can contribute to abate the global warming by absorbing carbon dioxide in the exhaust gas.

Further, sulfurous acid gas contained in the mixed gas used for the culture inhibits the growth of algae and bacteria other than the algae of interest, thus the algae of interest can be efficiently cultured as a dominant species.

Therefore, the algae culture method of the present invention is potentially a versatile culture method that enables to culture a wide variety of sulfurous acid gas-resistant algae, such method being considered as a prerequisite to achieving the production of a wide variety of organic materials by recovering carbon dioxide from the mixed gas containing carbon dioxide and sulfurous acid gas.

DESCRIPTION OF EMBODIMENTS

First Embodiment

Figure 1:
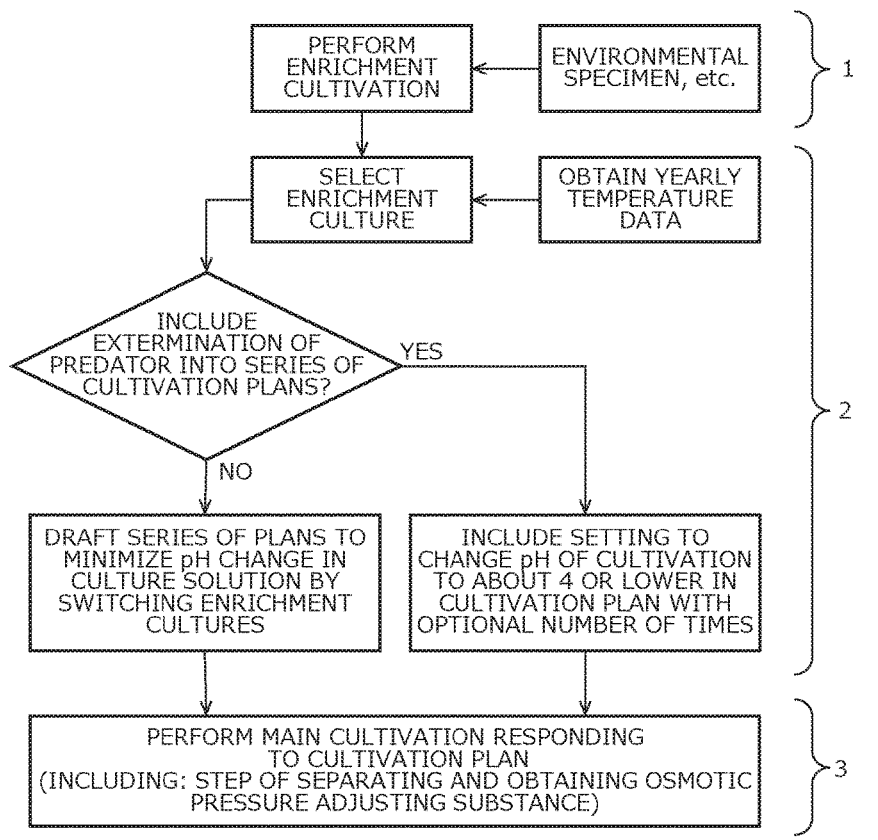
FIG. 1 is a conceptual diagram showing an implementation flow of a first embodiment of the present invention.

Hereinafter, an algae culture method and a production method of betaine and the like, according to a first embodiment of the present invention, will be described.

In the present specification, betaine refers to trimethyl glycine (N,N,N-trimethylglycine: $C_5H_{11}NO_2$) and is also known as glycine betaine, betaine anhydrous, TMG, and the like.

The algae culture method and the production method according to the present embodiment is a production method of betaine or glucosyl glycerol characterized by comprising:

an enrichment culture preparation step for preparing a plurality of enrichment cultures each including microalgae that contain betaine or glucosyl glycerol in an amount of 1 wt. % or more on a dry weight basis and having a different dominant species in microalgae flora by culturing an environmental specimen or a culture of microalgae derived from the environmental specimen under a photoautotrophic condition using a plurality of different culture conditions that include at least one of a temperature condition, a pH condition, and a salt concentration condition in which a final salt concentration in a culture is adjusted to 10 wt. % or more and 30 wt. % or less;

a cultivation plan step in which an optimum enrichment culture is selected from the plurality of enrichment cultures responding to an estimated temperature change and pH change caused in a medium during a main culture, and a series of culturing operations during the main cultivation are planned; and a main cultivation step for further producing a main culture that contains the microalgae containing the betaine or the glucosyl glycerol in an amount of 1 wt. % or more on a dry weight basis by performing the main culture under the photoautotrophic condition and the salt concentration condition of 10 wt. % or more based on the cultivation plan; and a step for separating and obtaining the betaine or the glucosyl glycerol from the main culture simultaneously with and/or after the main cultivation step.

The microalgae containing betaine or glucosyl glycerol of the present embodiment, described above, refer to microalgae that accumulate betaine or glucosyl glycerol in the algae bodies. As an environment where the microalgae containing betaine or glucosyl glycerol live, an environment having a water content with a solute concentration of approximately 10 wt. % or more can be mentioned.

Specifically, existence of such microalgae are confirmed in a natural environment, such as an intertidal zone, a salt-precipitate soil (salt land), a tide pool, and a hot spring, a side ditch of a crude oil drilling plant, a salt/sugar manufacturing plant, and the like, and an outdoor material storage space. The environmental specimen containing the microalgae are preferably collected from such places. The environmental specimen may be in a liquid or solid form. Further, the specimen may be collected at home and overseas, however it is recommended that the environmental specimen or the culture of microalgae derived from the environmental specimen is collected in the country where the main culture is performed. According to a non-patent literature, the microalgae usable for the present invention exist in abundance in the water and the soil of these collecting places. For example, Table 1 in NON-PATENT LITERATURE 1 (Journal of General Microbiology (1984), 130, 2177-2191. Mark A. Mackay et al.) shows that microalgae derived from an environment having a high salt concentration tend to contain betaine and the like inside the cells as an osmotic agent.

Further, the microalgae cultured by the algae culture method of the present embodiment may acquire a betaine or glucosyl glycerol synthesis ability congenitally or postnatally.

Examples of the microalgae having congenitally acquired the betaine or glucosyl glycerol synthesis ability include blue-green algae, such as *Halothece* genus, *Dactylococcopsis* genus, *Cyanothece* genus, *Spirulina* genus, *Halospirulina* genus, *Geitlerinema* genus, *Prochlorococcus* genus, *Synechococcus* genus, *Lyngbya* genus, *Moorea* genus, *Trichodesmium* genus, and *Oscillatoria*, red algae of *Galdieria* genus, as well as Pedinophyceae algae, Prasinophyceae algae, diatoms, and the like. These algae have a feature of containing betaine or glucosyl glycerol in the cells in response to a change in an external environment and the like, such as a salt concentration and a temperature of the culture solution.

It is noted that the microalgae having postnatally acquired the betaine or glucosyl glycerol synthesis ability may be used as the microalgae suitable for the culture of the present invention as long as the microalgae are capable of containing betaine or glucosyl glycerol in an amount of 1 wt. % or more on a dry weight basis of the algae bodies, thus the present invention is not limited to the particular species of microalgae and the like, described above. Further, in those microalgae, there is no particular limitation to an enzyme group, which plays a central role in the synthesis of betaine or glucosyl glycerol.

It is noted that, whether congenitally or postnatally, the microalgae containing betaine can exhibit, not only a salt resistance and/or a temperature resistance, but also a sulfurous acid gas resistance and a hydrogen sulfide gas resistance as an incidental effect. Thus, by using the microalgae described above, carbon dioxide can be recovered from a mixed gas containing carbon dioxide and sulfurous acid gas, such as an exhaust gas from coal-fired power stations, and further converted to betaine, which is a valuable substance.

Of the operating steps according to the first embodiment of the present invention, the enrichment culture preparation step 1 (FIG. 1) as a first operating step will be first described below.

In the present specification, the term "environmental specimen" refers to a specimen collected from a natural environment, including land water, such as rivers, lakes, soil water, and ground water, seawater, soil, and the like. The "environmental specimen" is not needed to be collected from a single collecting area, and may be a mixture of a plurality of the environmental specimens collected from a plurality of different collecting areas. Further, the term "culture of microalgae derived from the environmental specimen" refers to a culture containing microalgae that have been previously grown in the enrichment culture and stored, isolated microalgae, and the like. The microalgae having postnatally acquired the synthesis ability of betaine and the like are also included.

In this step, an "environmental specimen or a culture of microalgae derived from the environmental specimen" is first prepared.

Figure 2:
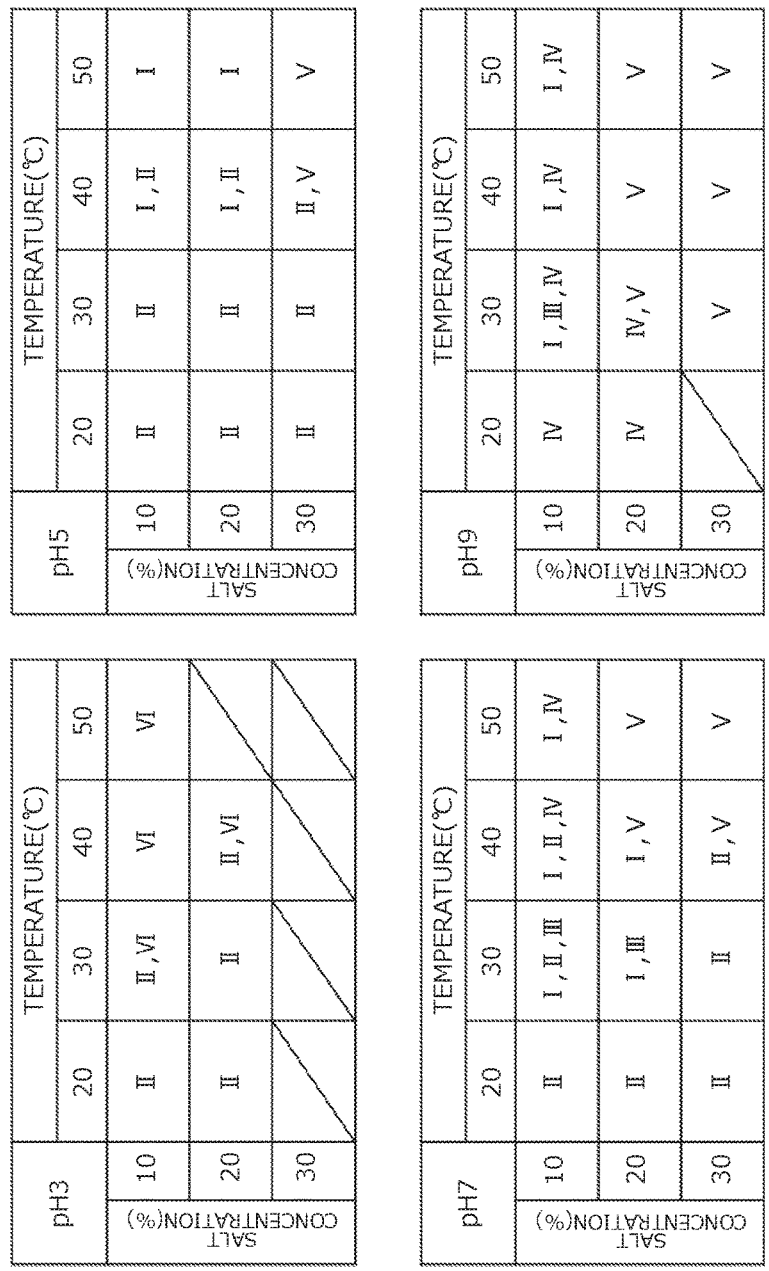
FIG. 2 is a diagram showing examples of enrichment cultures obtained in an enrichment culture preparation step of the first embodiment.

Next, culture conditions of the enrichment culture are set. A plurality of different culture conditions are set by combining, for example, one or a plurality of temperature conditions of 20° C. to 50° C., one or a plurality of pH conditions of pH3 to pH9, and one or a plurality of salt concentration conditions in which a final salt concentration for culturing is adjusted to 10 to 30 wt. %. FIG. 2 shows a result of Example 1 in which the enrichment culture was performed with the above setting. In this Example, four temperature conditions of 20, 30, 40, and 50° C., four pH conditions of pH3, 5, 7, and 9, and three salt concentration conditions of 10, 20, and 30 wt. % as the final salt concentration were set as the culture conditions and a total of 48 enrichment cultures were performed.

It is noted that a type of medium used for the enrichment culture is not particularly limited, but the medium is preferably the same as the one used for the main culture. Further, the present embodiment is characterized by performing a culture under a high salt condition. Salts used for adjusting the salt concentration may be substances of mixed salts mainly composed of NaCl, such as sea salts and rock salts. However, there is no particular limitation to salt constituents unless such salt constituents contain salts that significantly inhibit the growth of the microalgae in the culture.

Condition setting performed by changing the temperature, pH, and salt concentration conditions is an important requirement in the enrichment culture step of the microalgae containing betaine and the like of the present embodiment, however light quantity set as a fixed condition in the enrichment culture step is one of the culture conditions that is considered to be equally or more important than the foregoing requirement.

Specifically, when the present embodiment is carried out particularly in a region rich in the solar radiation energy, an irradiation condition of the enrichment culture is determined responding to a light quantity, which would be obtained by sunlight irradiation in a main cultivation step 3. This is because strong light irradiation, especially under a low temperature condition, is known to have a strong impact on the growth and survival of the microalgae. In carrying out the present invention designed for a year-round culture, it is important to obtain in advance an enrichment culture that can withstand the strong light irradiation under the low temperature condition and add it to a line up of the enrichment cultures, in order to stabilize the culture at the time when a day difference of growth, atmospheric temperature/water temperature, and the like is extreme, particularly in the cold winter, and to achieve a stable culture throughout the year.

According to the enrichment culture preparation step 1 described above, there can be obtained the enrichment cultures in which the microalgae containing betaine and the like dominate depending on the culture conditions used as growth conditions.

Subsequently, the cultivation plan step 2 (FIG. 1) as a second operating step will be described below.

This step comprises a first step in which an appropriate enrichment culture is selected responding to a temperature change in the medium expected to occur during the main cultivation and a second step in which, during a transition of the enrichment culture, the selected enrichment culture is optimized in a manner such that the transition of dominant species of the enrichment culture in transition can be smoothly carried out, and a total cultivation plan is drafted based on the plan in which the optimization is contemplated.

In the first step, a trend of temperature change of the culture solution associated with seasonal variation is accurately predicted and an appropriate enrichment culture is selected responding to the predicted trend. Specifically, when the past data on a temperature change of the culture solution throughout the year is available at the actual location or its vicinity, such data can be used. Further, when suitable data is not available, a trend of temperature change of the culture solution of the main culture is predicted as accurately as possible referring to the past data on a temperature change and the like stored in a local meteorological observatory.

For example, a simple moving average value and the like of the past data on atmospheric temperature and water temperature for certain periods in the past can be obtained by a common spreadsheet application and is thus the most convenient index to use.

Further, since the simple moving average value is obtained using the past data, action to the actual state is slightly delayed. However, in the time from winter to summer when the temperature is in an upward trend, the growth and metabolism of microalgae are also on the rise, thus the slight delay makes little difference.

On the other hand, in the time from summer to winter when the temperature is in a downward trend, the growth and metabolism of microalgae are also on the decline and the culture tends to become unstable. Further, the downward trend of the temperature differs depending on whether the culture takes place at a coast area or an inland area. Thus, when the temperature is in the downward trend, it is recommended to refer to a trend using lowest atmospheric temperature data and the like, of which temperature is further lower than the average atmospheric temperature trend.

It is noted that when the cultivation plan is drafted by referring to the above atmospheric temperature trend, or when an operation management is performed in a manner that a decision is locally made by creating a water temperature trend from actual data obtained by measuring an actual water temperature during the culturing operation, it is not necessary to precisely determine a turning point of the temperature trend from the rise to decline, the timing to change the enrichment culture, or the like. It is only required to grasp the changing tendency roughly as a medium to short term temperature trend, and it is not necessary to react each time to the simple moving average value that changes every day. The actual atmospheric temperature does not change monotonously upward or downward, besides, the trend differs from year to year.

The culturing business conducted on the above premise is highly dependent on environment. Thus, it is necessary to separately take sufficient measures to the risk of change in the temperature trend caused by deviating from the expectation or the plan.

One of the most effective measures is to improve the selection of the enrichment culture. Specifically, the enrichment culture in each temperature category is combined in a manner that the combined product has an overlapping species in microalgae flora constituting the enrichment culture before and after the change. In the selection of the enrichment culture from each temperature category in the Example shown in FIG. 4, the combination is made in consideration of having an overlap of a microalgae species contained in each culture.

This operation is formally intended to adjust the enrichment culture to cope with the risk of temperature change within a range of 10° C., but can practically work with temperature change within a range of 20° C.

It is noted that only specific elements are mentioned to describe the trend making method, the data selection, and the measures to the risk of changes, however the present invention is not limited to these specific examples.

Based on the temperature change trend of the culture solution predicted in the above, the suitable enrichment culture is selected responding to the temperature change from the plurality of the enrichment cultures obtained in the former step.

Next, in the second step, by referring to information on a dominant species of the enrichment culture that is determined to be suitable for the temperature change, a pH range that is preferred by the dominant species is estimated.

The description is hitherto made on the temperature of the culture solution that changes during a specified culture period, the selection of the optimum enrichment culture responding to the temperature change of the culture solution, and the estimation of the pH range that is preferred by the dominant species constituting the optimum enrichment culture. In a series of steps of successively changing the optimum enrichment cultures in the main cultivation plan, if the change of the optimum enrichment cultures causes a pH gap accompanied with an extreme pH change by referring to the pH that is preferred by the dominant species constituting the optimum enrichment culture, the operation plan of the optimum enrichment cultures is preferably altered so as to minimize the pH adjustment in the culture solution.

When the main culture is performed in a batch culture, the pH can be adjusted each time when the culture is prepared. However, performing a continuous culture requires a slow change of the microalgae flora and a slow change of the pH according thereto. Basically, the optimized enrichment culture is preferably selected so as to avoid an extreme pH change that causes a rapid shift from alkaline to acidic state.

A conventional commercial production of microalgae are performed by a monoculture in which one specified microalgae strain is cultured. Thus, the culture period and the culture method are limited by growth temperature characteristic of the specified microalgae. Further, the monoculture has a feature of being significantly damaged by a predatory organism.

Commercial production of the microalgae of the present invention is characterized by being performed with a stance in that the production is focused on an end product and not limited to microalgae. Thus, the production of the present invention can cope with a wide range of temperatures. Further, the production of the present invention is based on the changes in the culture conditions and thus characterized by stabilizing the productivity of the end product by reducing the damage caused by predators by changing the conditions and the like. Therefore, the cultivation plan step 2 as the second operating step is considered to be a particularly important step for not only stabilizing the microalgae culture, but also stabilizing the productivity of the end product.

Finally, the main cultivation step 3 (FIG. 1) as a third operating step will be described below.

The main cultivation step 3 can be carried out in accordance with a mass culture method used in the conventional commercial production of microalgae, such as an open pond method, a raceway method, a tube method, a floating film method, and a thin layer or flat panel method.

It is noted that the culture method of the present invention adopts a multiculture method in which an appropriate enrichment culture is selected responding to a local temperature trend and the selected enrichment culture is cultured with its optimum conditions to achieve a long-term culture, and is thus different from a conventional culture method based on a monoculture.

Such culturing operations are carried out with particular attention to the pH adjustment. The pH adjustment follows the previously described cultivation plan. The pH adjustment method may be carried out by a diluted acid/alkali solution or blowing of carbon dioxide. However, in consideration of a slow progress of the temperature change trend, the pH is mildly adjusted utilizing a gentle pH transition due to the consumption of medium components used in the culture.

For example, when the culture is carried out using an MC medium, since a normal MC medium contains potassium nitrate as a nitrogen source, the use of this nitrogen source causes the culture solution to shift to an alkali side along with the progress of culturing. In order to shift pH of the culture solution to an acidic side, ammonium chloride, ammonium sulfate, and the like are used instead of potassium nitrate (however, it is reported that a high concentration of ammonium salts inhibits the photosynthesis of microalgae, thus attention should be paid to an apply concentration). Adjustment of pH is performed appropriately in accordance with the temperature change trend by taking into consideration an amount of ammonium salts necessary for achieving the desired pH setting and an amount of ammonium salts used for a single round of culture.

Further, in the main cultivation step 3, as is performed in a second embodiment, a mixed gas containing sulfurous acid gas and carbon dioxide is blown to the culture solution in which the enrichment culture containing the microalgae grow, thereby allowing the microalgae to perform photosynthesis to recover carbon dioxide from the mixed gas and convert carbon dioxide to organic materials. Detailed methods and conditions in this process will be described in the second embodiment below.

It is noted that the microalgae produced in the main cultivation step 3 are separated from the culture solution and further subjected to an operation of extracting betaine and the like from the algae bodies.

These processes employ different methods depending on the microalgae species produced through out the year. Thus, different methods are set each time in consideration of cost-effectiveness. It is noted that, as a versatile method for separating the algae bodies from the culture suspension, centrifugal separation, pressure floatation, flocculation precipitation, and the like can be mentioned. In this process, the culture solution separated from the algae bodies is basically returned to the culture tank again.

Further, extraction of betaine and the like from the algae bodies is generally performed by a method using a solvent such as alcohol, and the like. The extraction efficiency can be improved in combination with a physical cell disruption method, such as freeze-thaw, freezing crushing, and ultrasonic crushing. Further, by utilizing the fact the salt concentration in the main culture of the present invention is high, the algae bodies are added with a small amount of a hypotonic solution to swell the cells and then the above physical cell disruption method may be applied.

Overall, betaine and the like are separated from the microalgae by performing a combination of such methods.
<Knowledge and Idea as Prerequisite for Second Embodiment>

It is conventionally known that microalgae of *Galdieria* genus are resistant to sulfurous acid gas. However, it has been entirely unknown what mechanism causes the sulfurous acid gas resistance. Under these circumstances, the present inventors collected water or soil specimens containing microalgae from a plurality of regions at home and overseas. When the microalgae were inoculated into a culture solution blown with a gas containing hydrogen sulfide, sulfurous acid gas, and carbon dioxide for culturing, a large number of enrichment cultures having resistance to these toxic gases could be easily obtained.

The reason for mixing hydrogen sulfide into the blowing gas was an expectation to obtain algae, which were clearly different from the conventional algae having resistance to sulfurous acid gas. Another reason was that, as a result of analyzing the genome information of recently published algae and plants, the following could be predicted: it was likely that sulfurous acid gas was metabolized to hydrogen sulfide by sulfite reductase in the algae bodies; and algae having resistance to hydrogen sulfide might have more excellent resistance to sulfurous acid gas than algae not having resistance to hydrogen sulfide gas.

The above enrichment cultures obtained in this manner were observed with a microscope and classified into seven enrichment cultures that include, as a dominant microalgae species, *Spirulina* genus, *Halothece* genus, *Geitlerinema* genus, and *Galdieria* genus (details are shown in Table 1 below).

A common feature of these enrichment cultures having resistance to hydrogen sulfide gas and sulfurous acid gas was to contain betaine (trimethyl glycine or glycine betaine) in the algae bodies, specifically betaine in an amount of 1 wt. % or more on a dry weight basis of the algae bodies.

Based on these culture results, the published genome information on the microalgae strain of *Galdieria* genus was once again examined. Surprisingly, it was found that an FTSH-Zn enzyme gene involved in the metabolism and re-synthesis of a photosynthesis-related protein (D1 protein), which was a target of hydrogen sulfide, was encoded on the same operon as a betaine synthetase gene. Therefore, it was speculated that accumulation of betaine in the algae bodies and resistance to hydrogen sulfide, which was generated by metabolizing sulfurous acid gas in the algae bodies (i.e., resistance to sulfurous acid gas), were closely related.

Based on these findings, the present inventors came up with the idea that, besides the algae of *Galdieria* genus, which were conventionally known to be resistant to sulfurous acid gas, any microalgae that had a ability to contain betaine in the algae bodies could be resistant to hydrogen sulfide gas and sulfurous acid gas, and thus completed the present invention.

Second Embodiment

Hereinafter, the present invention will be described further in detail based on preferred embodiments. A culture of the present embodiment may be carried out in the main cultivation step 3 (FIG. 1) of the first embodiment.

A second embodiment of the algae culture method according to the present invention is an algae culture method in which a mixed gas containing sulfurous acid gas and carbon dioxide is blown to a culture solution of algae that contain betaine in an amount of 1 wt. % or more on a dry weight basis of the algae bodies to allow the algae to grow and perform photosynthesis, thereby recovering carbon dioxide from the mixed gas and converting carbon dioxide to organic materials.

In the algae culture method of the present embodiment, it is highly unlikely that other microalgae that do not contain betaine and bacteria exhibit sulfurous acid gas resistance. Thus, even when an extensive mass culture is performed outdoors, probability for having contamination with microorganisms such as undesired microalgae are extremely low. Consequently, both the purity and productivity of biomass obtained from the desired algae can be easily maintained very high.

The algae used in the present embodiment are preferably resistant to hydrogen sulfide gas from the findings described above. The algae having such resistance are likely to contain betaine, which is strongly involved in sulfurous acid gas resistance, in an amount of 1 wt. % or more on a dry weight basis of the algae bodies, thus may exhibit the further excellent sulfurous acid gas resistance.

The algae used in the present embodiment are preferably resistant to sulfurous acid gas. The mixed gas blown to the culture solution contains sulfurous acid gas, thus culture efficiency (growth efficiency) of the algae is, needless to say, improved by having sulfurous acid gas resistance.

It is noted that sulfurous acid gas (sulfur dioxide: $SO_2$) reacts with water molecules in the culture solution to generate sulfurous acid ($H_2SO_3$). Thus, in the present invention, sulfurous acid gas resistance has the same meaning as sulfurous acid resistance.

In the algae culture method of the present embodiment, a betaine content of the algae bodies of the microalgae are preferably operated by adjusting the culture conditions.

For example, the salt concentration with respect to the total weight of the culture solution (excluding the weight of algae being cultured) is preferably adjusted to 3 to 30 wt. %.

Specifically, by setting the salt concentration to, for example, 10 to 30 wt. %, 10 to 25 wt. %, 12.5 to 22.5 wt. %, or 15 to 20 wt. %, the microalgae exhibit or acquire an ability to accumulate betaine, thereby increasing the betaine content in the algae bodies and having a tendency to improve sulfurous acid gas resistance.

The salts in the culture solution herein are a substance made from mixed salts mainly composed of NaCl, such as sea salts and rock salts. There is no particular limitation to salt constituents unless such salt constituents contain salts that significantly inhibit the growth of the microalgae in the culture. Further, a method of adjusting the salt concentration include a method based on a combination of increasing the salt concentration by evaporation of the culture solution and by adding the mixed salts mainly composed of NaCl, such as sea salts and rock salts, refined salts, or the like, and diluting the salt concentration by using seawater, fresh water, or the like, having the lower salt concentration than the culture solution.

The salt concentration in the culture solution can be measured by a method using a refraction-type salt concentration meter.

In the algae culture method of the present embodiment, the growth of undesired microorganisms contaminated in the culture solution can be prevented by blowing a mixed gas containing sulfurous acid gas at a concentration of 5 ppm or more with respect to the total volume of the mixed gas to the culture solution.

In the algae culture method of the present embodiment, as the mixed gas blown to the culture solution, an exhaust gas generated by burning a sulfur-containing substance can be used. Such an exhaust gas usually contains sulfurous acid gas and carbon dioxide at a high concentration enough to cause damage to plants, even after the exhaust gas is subjected to a desulfurization treatment. The exhaust gas may be diluted by mixing with an air in order to dilute the concentrations of sulfurous acid gas and carbon dioxide in the exhaust gas to a level in which the growth of the microalgae are not prevented. Further, the mixed gas may contain a gas other than sulfurous acid gas and carbon dioxide.

Figure 3:
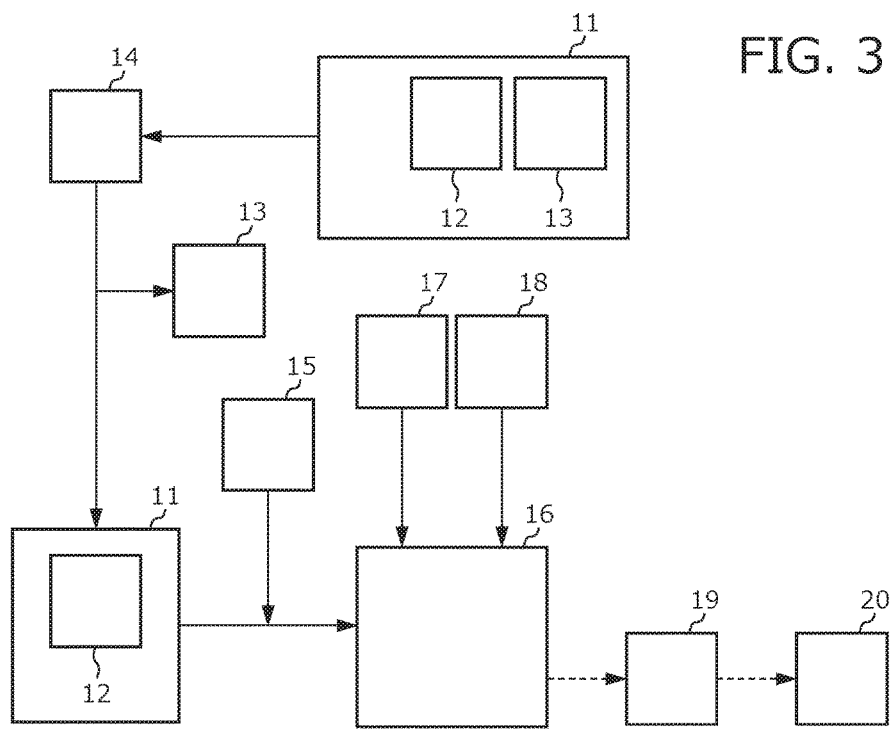
FIG. 3 is a schematic view showing a process of recovering carbon dioxide from a mixed gas containing sulfurous acid gas and carbon dioxide using a conventional culture system of microalgae.
Figure 4:
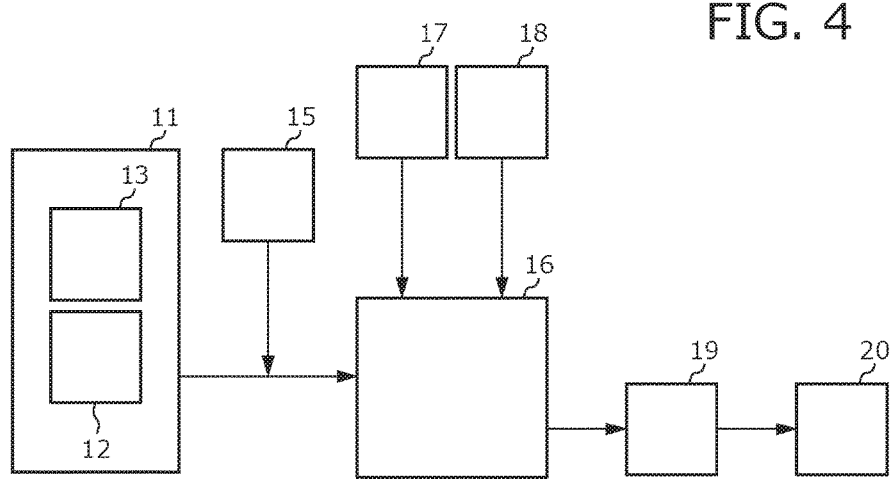
FIG. 4 is a schematic view showing one example of a process of recovering carbon dioxide from a mixed gas containing sulfurous acid gas and carbon dioxide using a culture system of microalgae according to a second embodiment of the present invention.

According to the algae culture method of the present embodiment, when the exhaust gas discharged from an apparatus or facility, which burns fuel containing a sulfur-containing substance, such as a thermal power plant, is used as the mixed gas supplied to a mass culture of the microalgae, a high-cost treatment for sulfurous acid gas (desulfurization apparatus 14), which is previously required (see FIG. 3), is not necessary in a step prior to the blowing of the exhaust gas (see FIG. 4). Thus, the mass culture of the microalgae can be achieved at a low cost. By this, it also becomes possible to produce industrially useful organic materials.

The betaine content in the microalgae on a dry weight basis of the algae bodies can be measured by a separation/detection method using a high performance liquid chromatography after subjecting dried microalgae in a prescribed amount to ethanol extraction and separating an extract solution from the algae bodies by centrifugation or a filtering operation.

The upper limit of the betaine content is not particularly limited, however it is not normally greater than 30 wt %. The microalgae containing 1 wt % or more of betaine can be expected to be resistant to sulfurous acid gas contained in the blown gas in an amount of at least 1 ppm or more.

Higher resistance to sulfurous acid gas is more preferable, however it is normally considered to be difficult to exhibit resistance to the blown gas containing sulfurous acid gas at a concentration exceeding 1000 ppm.

From the viewpoint of improving sulfurous acid gas resistance, the betaine content in the microalgae to be cultured on a dry weight basis of the algae bodies is preferably 1 to 30 wt. %, more preferably 3 to 30 wt. %, further preferably 15 to 30 wt. %.

The microalgae cultured by the algae culture method of the present embodiment may acquire a betaine synthesis ability congenitally or postnatally. Alternatively, the microalgae may acquire an ability to take betaine into the algae bodies from a culture environment congenitally or postnatally.

As for the microalgae having congenitally acquired the betaine synthesis ability, the microalgae having postnatally acquired the betaine synthesis ability, or the microalgae having congenitally or postnatally acquired the ability to take betaine into the algae cells from the culture environment by the action of a betaine transporter and the like of the cell surface, the species of the microalgae are not limited. That is, the microalgae can be preferably used in the present invention as long as they are capable of containing 1 wt. % or more of betaine on a dry weight basis of the algae bodies. In these microalgae, an enzyme group playing a central role in the synthesis or the incorporation of betaine is not particularly limited.

Examples of the microalgae having congenitally acquired the betaine synthesis ability include blue-green algae, such as *Halothece* genus, *Dactylococcopsis* genus, *Cyanothece* genus, *Spirulina* genus, *Halospirulina* genus, *Geitlerinema* genus, *Prochlorococcus* genus, *Synechococcus* genus, *Lyngbya* genus, *Moorea* genus, and *Trichodesmium* genus, and red algae, such as *Galdieria* genus. These microalgae have a property of containing betaine in the cells in response to an external environmental change and the like, such as the salt concentration and the temperature in the culture solution.

Further, the microalgae, in which a gene capable of postnatally conferring the betaine synthesis ability is introduced by gene recombination and the like, are not limited to the above taxonomic group.

It is noted that, whether congenitally or postnatally, the microalgae containing betaine can not only exhibit sulfurous acid gas resistance and hydrogen sulfide gas resistance, but also improve salt resistance and/or temperature resistance as an incidental effect. Thus, by using the microalgae described above, a mass culture strong against cultural environment changes can be stably performed.

The microalgae to be cultured by the algae culture method of the present embodiment may be an enrichment culture, which is obtained by inoculating water or soil collected from a natural environment where the microalgae inhabit into the culture solution blown with a mixed gas containing carbon dioxide and at least one of sulfurous acid gas and hydrogen sulfide gas, and selecting microalgae which succeeded in growing in the culture.

According to the algae culture method in which the enrichment culture is obtained and cultured in this manner, the desired algae (enrichment culture) exhibiting sulfurous acid gas resistance can be efficiently cultured as a dominant species. Further, such a culturing method can eliminate the labor and time for isolating in advance a single specific strain of the algae resistant to sulfurous acid gas. In addition, the selected enrichment culture seems to include a plurality of algae species capable of mutually supporting their growth or survival, thereby enabling to achieve the culture highly resistant to changes in the culture conditions.

As the natural environment where the microalgae to be cultured in the present embodiment can be collected, relatively high salt concentration environments are preferred. Specifically, an intertidal zone, a salt-precipitate soil (salt land), a tide pool, an acidic hot spring, and the like are preferable as collecting areas of the microalgae. Further the collecting areas may be at home and overseas.

It has been found, by the non-patent literature, that the microalgae usable for the present embodiment exist in abundance in the water and the soil of these collecting areas, as described above. The above microalgae can be obtained by a well-known collecting method. Further, as the culture solution (medium) and the culture conditions necessary for culturing the desired microalgae, well-known culture solution and culture conditions for culturing microalgae are applicable.

In the algae culture method of the present embodiment, the size and form of the culture are not particularly limited. The size and form of the culture can be adjusted appropriately in accordance with the property of the microalgae to be used and the purpose of the culture, for example, from a small culture scale using an incubator connected to a resin tube or hose to a large culture scale using an outdoor culture tank of which one side is in kilometer size.

EXAMPLE

The enrichment culture preparation step according to the first embodiment will be described further in detail below based on a case of the enrichment culture, in which the present embodiment was performed with the assumption that commercial production would be carried out in Oman.

Example 1 (First Embodiment)

In order to create an enrichment culture to be used for a verification test in Oman, environmental specimens were collected in the following areas in Oman.

[1] Fifteen bottom mud specimens collected from 12 mangrove tidelands

[2] Surface soil specimens collected from 13 salt plains in the Umm as Samim area

[3] Fourteen water and algae mat specimens from 11 salt pans and tide pools having a high salt concentration (about 20%) in the Barr Al-Hikman area

[4] Four sludge and algae mat specimens collected from 2 high-temperature acidic drains of wastewater from a crude oil refining plant In a culture solution of the enrichment culture, an MC medium prepared by seawater was used as a basic medium, and the salt concentration was adjusted by adding NaCl and pH was adjusted by adding 0.1 mol/L of hydrochloric acid solution or sodium hydroxide solution. It is noted that four temperature conditions of 20, 30, 40, and 50° C., four pH conditions of pH3, 5, 7, and 9, and three salt concentration conditions of 10, 20, and 30 wt. % as a final salt concentration were set as the enrichment culture conditions to perform a total of 48 enrichment cultures.

Inoculation of the environmental specimens into each enrichment culture was performed by suspending 0.1 g of each specimen into 50 ml of the culture solution used for each enrichment culture. After sufficiently stirred, the suspension was left to stand for 10 min and then 25 ml of supernatant was inoculated into 75 ml of each culture solution to prepare 100 ml of specimen suspension. After being prepared, the specimen suspension was transferred to a sterile conical flask with a 300 ml volume and placed in a constant temperature incubator set at a specific temperature. The specimen suspension was subjected to the enrichment culture for about 3 weeks under an artificial solar light irradiation condition creating a photon flux density of about 2 mmol·m$^{-2}$·s$^{-1}$ using a metal halide lamp installed in an upper portion of the incubator.

Results of the enrichment cultures are shown in FIG. 2. Morphological observation of the microalgae in the enrichment cultures confirmed that microalgae flora is generally formed by filamentous blue-green algae, Pedinophyceae algae (eukaryote, characterized by having a single flagella), spiral-shaped blue-green algae, spherical blue-green algae, rod-shaped blue-green algae, and red algae (eukaryote, characterized by having blue-green color) in the enrichment cultures. Further, observation results of microalgae compositions in each enrichment culture are shown in FIG. 2.

In pH3, red algae became a dominant species with the salt concentration of 10 wt. % and the temperatures of 40 and 50° C., Pedinophyceae algae became a dominant species with the temperatures of 20 and 30° C. or the final salt concentration of 20 wt. %, while no microalgae could grow with the final salt concentration of 30 wt. % in all temperature ranges.

In pH5, Pedinophyceae algae became a dominant species with the temperatures of 20, 30 and 40° C. in all salt concentration categories. Further, filamentous blue-green algae became a dominant species with the temperatures of 40 and 50° C. and the final salt concentrations of 10 and 20 wt. %.

In pH7, Pedinophyceae algae tended to become dominant with the temperatures of 20 and 30° C. and filamentous blue-green algae tended to become dominant with the salt concentrations of 10 and 20 wt % and the temperatures of 30, 40 and 50° C., however various microalgae became dominant depending on the conditions in other categories.

In pH9, spherical blue-green algae tended to become dominant with the salt concentrations of 10 and 20 wt. % in all temperature ranges. Further, rod-shaped blue-green algae tended to become dominant with the temperatures of 30, 40 and 50° C. and the salt concentrations of 20 and 30 wt. %.

In this manner, a wide variety of enrichment cultures having different microalgae compositions were obtained responding to the culture conditions by performing a number of enrichment cultures. Nothing grew in some condition categories, however, at least in the condition categories in which the growth of the microalgae was confirmed, all enrichment cultures were confirmed to contain betaine in an range of 1.4 wt. % or more and 2.4 wt. % or less on a dry weight basis of the enriched microalgae responding to an HPLC analysis (FIG. 5).

Figure 5A:
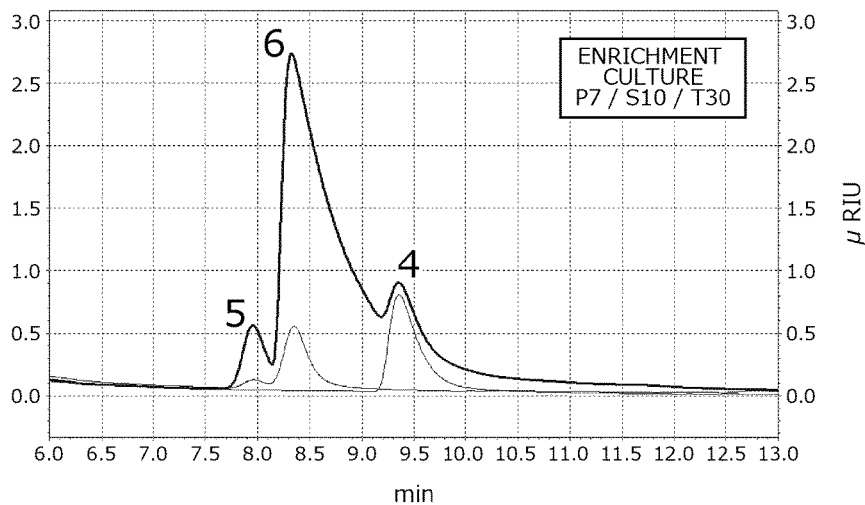
FIGS. 5A and 5B are graphs showing a result of an HPLC analysis of osmotic pressure adjusting substances in the enrichment cultures of the first embodiment.
Figure 5B:
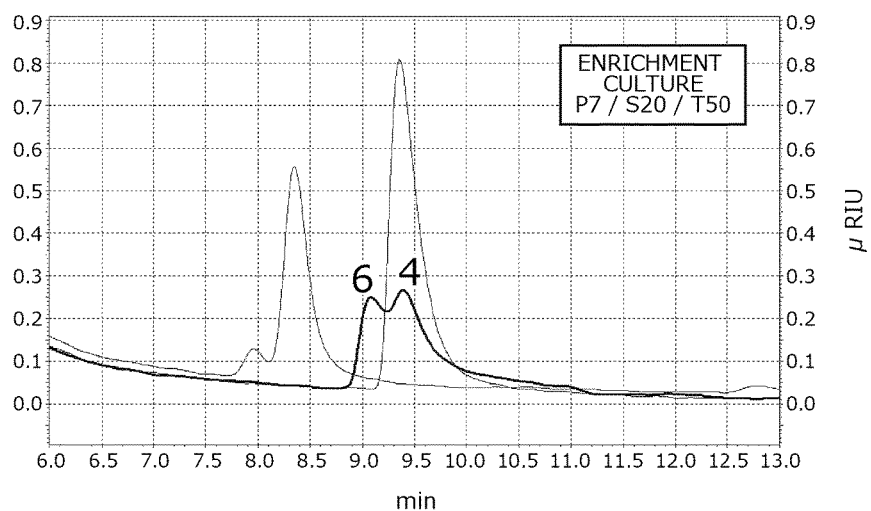

Further, as shown in FIG. 5, the presence of the enrichment culture, which produced glucosyl glycerol in addition to betaine, was suggested. Glucosyl glycerol is also one of valuable substances used as a moisturizing agent and as an active ingredient in cosmetics. This confirmed that, according to the present invention, an osmotic pressure adjusting substance, such as glucosyl glycerol, could be produced, besides betaine.

The enrichment cultures, which were confirmed to contain betaine and the like, were subjected to subcultures every two weeks under the appropriate enrichment culture conditions to make stocks of the enrichment culture lines.

Example 2 (First Embodiment)

Based on the enrichment culture results shown in FIG. 2, the steps 1 and 2 in the cultivation plan step were performed under the assumption that there was a change in the water temperature of the culture from 20° C. to 50° C. in the transition of season from winter to summer. It is noted that the enrichment culture used in each temperature range were selected under the assumption that a pH variation in the culture was suppressed in a certain range by alternately using potassium nitrate and ammonium sulfate for adjusting pH. It is noted that the salt concentration was fixed to 20 wt. %.

Figure 6:
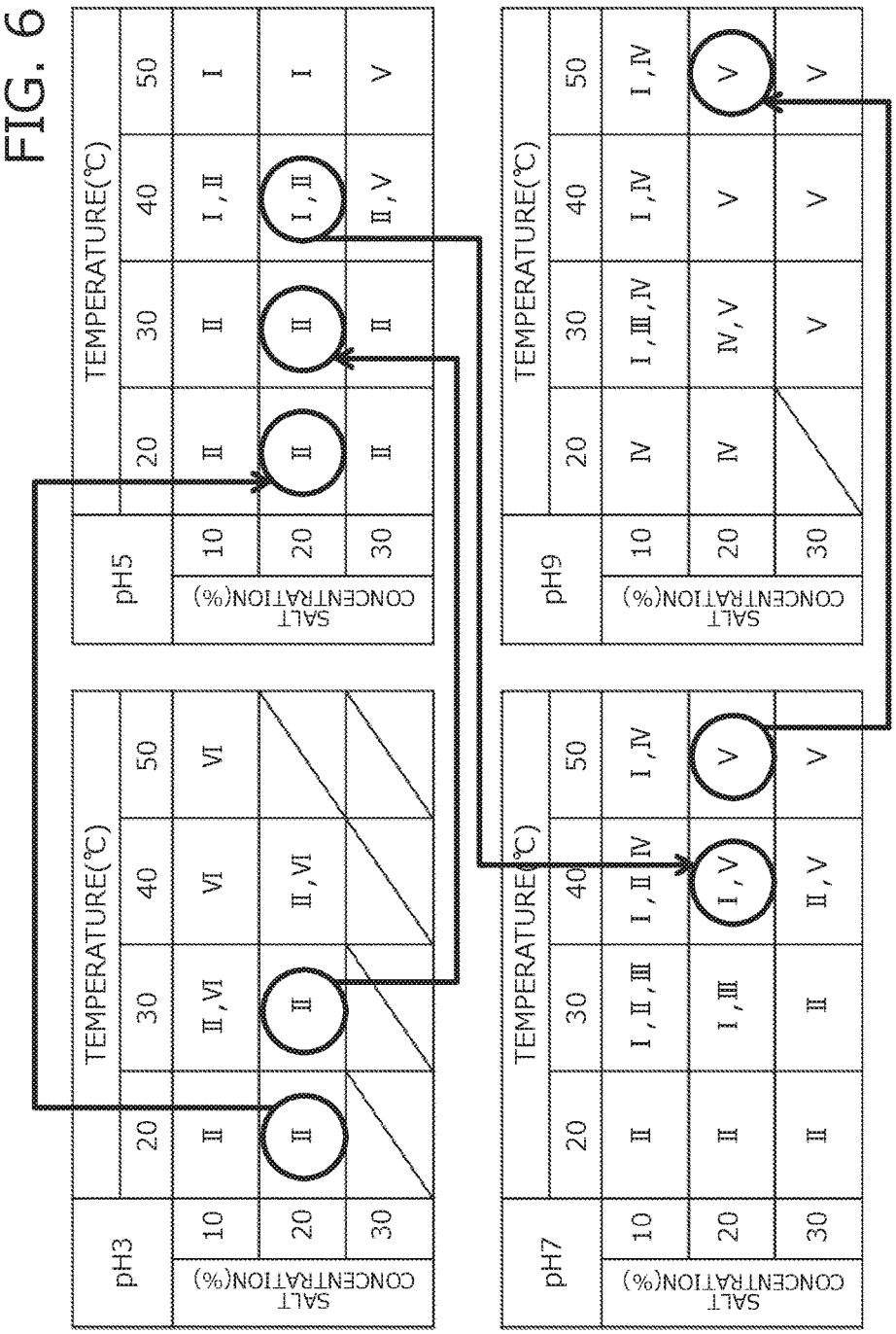
FIG. 6 is a diagram showing a selection example of the enrichment cultures in a cultivation plan step of the first embodiment.

The enrichment culture used in each temperature range was selected by focusing on the dominant species in the enrichment culture obtained under each of the conditions. The results were shown in FIG. 6.

In the culture at the temperature of 20° C., a plan was drafted as follows: two enrichment cultures P3/S20/T20 (the term representing a culture enriched under the conditions of pH3/salt concentration of 20 wt. %/temperature of 20° C., hereinafter, the enrichment culture is represented in the same manner) and P5/S20/T20 were mixed to use in a range of pH3 and pH5. This enrichment culture mixture was generally dominated by Pedinophyceae algae.

Next, in the culture at the temperature of 30° C., a plan was drafted as follows: two enrichment cultures P3/S20/T30 and P5/S20/T30 were mixed to use in a range of pH3 and pH5. This enrichment culture mixture was generally dominated by Pedinophyceae algae, as in the case of 20° C.

Further, in the culture at the temperature of 40° C., a plan was drafted as follows: two enrichment cultures P5/S20/T40 and P7/S20/T40 were mixed to use in a range of pH5 and pH7. This enrichment culture mixture contained Pedinophyceae algae and rod-shaped blue-green algae, but was dominated by filamentous blue-green algae. Thus, a plan was drafted such that the dominant species was switched from Pedinophyceae algae, which was a dominant species in the culture from 20° C. to 30° C., to filamentous blue-green algae.

Further, in the culture at the temperature of 50° C., a plan was drafted as follows: two enrichment cultures P7/S20/T50 and P9/S20/T50 were mixed to use in a range of pH7 and pH9. This enrichment culture mixture was dominated by rod-shaped blue-green algae. Thus, a plan was drafted such that the dominant species was switched from filamentous blue-green algae, which was a dominant species in the culture at 40° C., to rod-shaped blue-green algae.

In the above setting, where the dominant species changed depending on the temperature, the selection of the preceding enrichment culture was made under the assumption that the dominant species changed. That is, in order to achieve a smooth transition, a consideration was made so as to select the preceding enrichment culture that contained the microalgae predicted to be a dominant species in the following temperature setting.

It is noted that the change of the enrichment culture during the transition from winter to summer was performed based on the following plan: an average value of the highest temperatures in the past two weeks were obtained based on highest temperature data in the past two weeks and the enrichment culture was changed each time when the average value exceeded 30° C. and 40° C.

The timing of the change of the enrichment culture was predicted using the highest temperature data of the past weather observation data in Muscat (Oman). As a result, the timing of the change of the enrichment culture for 20° C. to 30° C. was predicted to be late March to early April and the timing of the change of the enrichment culture for 30° C. to 40° C. was predicted to be late May to early June. Further, a change to the enrichment culture for 50° C. was considered responding to the actual water temperature, however its application remained preliminary in the plan.

Overall, a selection method of the enrichment cultures at the transition from winter to summer, during which the water temperature of the culture increased from 20° C. to 50° C., was planned in the above.

It is noted that the above plan was drafted for the purpose of maximizing the productivity of the microalgae as a culture target. However, the productivity of the microalgae are sometimes significantly reduced in the actual culture due to predation by protozoa and the like, and other contamination. Thus, it is always necessary to include a concrete measure for the contamination in the cultivation plan.

In particular, cautions have to be taken in the temperature range from 20° C. to 40° C., since the contamination microorganisms, such as protozoa as predators, have the growth condition in the same temperature range. Empirically, damages caused by predation by the protozoa tend to be reduced by shifting pH to an acidic condition of pH4 or lower. Thus, as a solution for the contamination, a series of the cultivation plans may include in advance a step in which the culture solution is intentionally shifted to an extremely acidic condition on a regular basis. The plan shown in FIG. 6 includes a step of culturing at pH3 in order to avoid the effect of the predators.

As described above, in the cultivation plan step as the second operating step, the outline of applicability of commercial production, along-term schedule, running costs, and required time/quantity of necessary materials can be imaged in most of the parts before performing the main culture. In the conventional mass cultureion, the ongoing culture data were monitored in detail, however it was rare to predict the culture environment in a long span and carry out the cultivation plan based on the prediction. The reliable and stable culture based on the prediction of the culture environment is ensured by a group of the enrichment cultures obtained in the enrichment culture step. In the present invention, a highly reliable cultivation plan is drafted by placing emphasis particularly on the cultivation plan step, thereby enabling to carry out the stable commercial production culture for a long period.

In the above, the specific implementation examples and implementation methods of the first embodiment of the present invention were described with reference to FIG. 1, FIG. 2, FIG. 5 and FIG. 6. However, the present invention is by no means limited to these specific examples. It is needless to say that various modifications and additions can be made within the scope of the present invention.

Example 3 (Second Embodiment)

In the following, regarding a second embodiment, described is the background of how the inventors came to demonstrate that the betaine was contained in the microalgae and the content of betaine was involved in sulfurous acid gas resistance and hydrogen sulfide gas resistance in the microalgae.

The microalgae exhibiting a desired resistant phenotype were collected in a hot spring in Japan and a beach and a high salt environment (salt lake or salt land) in Oman.

A primary screening was performed under a culture condition in which hydrogen sulfide at 10 ppm was blown. A culture solution was prepared using an aqueous solution containing an MC medium and Daigo's artificial seawater SP (Wako Pure Chemical Industries, Ltd.), to which NaCl was further added to adjust the salt concentration to 10 wt. % with respect to the total weight of the culture solution. The salt concentration was determined by simulating mass culture conditions in a beach area, desert, and the like in the Middle East, where a large amount of water was evaporated from the culture solution. The screening of viable microalgae was performed at the culture temperature of 40° C. by intermittently blowing, to the culture solution, nitrogen containing 0.5% carbon dioxide, 1% oxygen, and 10 ppm hydrogen sulfide gas at a rate of 0.01 vvm on average under a continuous light irradiation condition in which light was irradiated using a white fluorescent lamp having an irradiation intensity of about 100 $\mu mol \cdot m^{-2} \cdot s^{-1}$ for 24 hours.

Screening results showed that a number of enrichment cultures resistant to hydrogen sulfide gas were obtained from specimens (water containing microalgae and salts) collected from 373 areas in two countries. Of these enrichment cultures, characteristics of seven enrichment cultures are shown in Table 1 as a specific example.

TABLE 1

Examples of enrichment cultures resistant to hydrogen sulfide gas obtained by screening

|  | BAH9 | BAH11 | BAH14 | SHN2 | NAG4 | GUN3 | AKI4 |
|---|---|---|---|---|---|---|---|
| Collection area | Intertidal zone | Salt land | Salt land | Tide pool | Acidic hot spring | Acidic hot spring | Acidic hot spring |
|  |  | Oman |  |  | Japan |  |  |
| Color tone of culture | Blue-green | Blue-green | Blue-green | Blue-green | Blue-green | Blue-green | Blue-green |
| Dominant species | Spirulina-like | Halothece-like | Halothece-like | Geitlerinema-like | Galdieria-like | Galdieria-like | Galdieria-like |
| Growth salt concentration (wt. %) | 5-20 | 10-30 | 10-30 | 3-20 | 0-10 | 0-10 | 0-15 |
| Growth temperature (° C.) | 35-45 | 30-45 | 30-45 | 20-55 | 20-55 | 20-55 | 20-55 |

The enrichment cultures resistant to hydrogen sulfide gas obtained by the primary screening were further examined whether they were resistance to sulfurous acid gas under the above culture conditions in which hydrogen sulfide gas was replaced with sulfurous acid gas. As a result, it was found that all the enrichment cultures were resistant to sulfurous acid gas and there was a close connection between hydrogen sulfide gas resistance and sulfurous acid gas resistance.

Next, sulfurous acid gas resistance (0, 5, 10, and 50 ppm) of each enrichment culture was examined, specifically with the following method. The enrichment cultures were grown in an aerated culture using a jar fermenter having a volume of 10 L in which a pH-stat setting is available. The culture was irradiated from a side by fluorescent lighting having a photon flux density of 150 µmol·m$^{-2}$·s$^{-1}$. A culture solution was prepared using an aqueous solution mainly containing the MC medium and Daigo's artificial seawater SP (Wako Pure Chemical Industries, Ltd.). The pH of the culture solution was adjusted to pH4 with diluted sulfuric acid and then further adjusted to pH8 by adding sodium carbonate. The pH of the culture solution after starting the culture was adjusted in a range of pH6 to 7 by blowing an air containing carbon dioxide and sulfurous acid gas.

Sulfurous acid gas resistance of each enrichment culture was examined in detail by changing pH, temperature, salt concentration, and carbon dioxide concentration, while using the above culture conditions as a basic condition. As a result, different behavior was observed in terms of sulfurous acid gas resistance depending on the salt concentration in the culture. As a representative example, a result of enrichment culture BAH11 is shown in Table 2. In Table 2, a peak culture concentration of the enrichment culture BAH11 is indicated by a numerical value of PCV (packed cell volume: ml/L) in a combination of the salt concentration and the sulfurous acid gas concentration blown. A higher value of PCV indicates a higher growth ability of the enrichment culture BAH11.

It was found that the enrichment culture BAH11 could grow in a wide range of the salt concentrations from 5 to 30 wt. %, however the sulfurous acid gas resistance was lost at the salt concentration of 12.5 wt. % or less with the salt concentration of about 12.5 wt. % as a border. Further, it was observed that when the salt concentration was 12.5 wt. % or more, as the salt concentration increased, sulfurous acid gas resistance also tended to increase.

TABLE 2

Changes of sulfurous acid gas resistance in enrichment culture BAH11

| | | Salt concentration (wt. %) | | | | | |
|---|---|---|---|---|---|---|---|
| | | 5 | 7.5 | 10 | 12.5 | 15 | 17.5 | 20 |
| Sulfurous acid gas concentration (ppm) | 0 | 4.3 | 7.8 | 12.5 | 11.2 | 10.5 | 10.2 | 4.3 |
| | 5 | 0.2 | 0.3 | 2.3 | 9.9 | 9.6 | 12.9 | 3.2 |
| | 10 | 0.2 | 0.8 | 0.4 | 5.1 | 10.8 | 10.5 | 3.8 |
| | 50 | 0.3 | 0.3 | 0.3 | 3.3 | 11.5 | 8.9 | 4.1 |

Values in table represent peak culture concentration: PCV (ml/L)

This observation result suggested a causal relationship between an osmotic agent in the cell and sulfurous acid gas resistance.

An intracellular osmotic pressure adjusting substance was examined under each salt concentration condition using $^{13}$C-NMR to find that the intracellular osmotic pressure adjusting substance was shifted from glucosyl glycerol to betaine with the salt concentration of about 12.5 wt. % as a border. Further it was confirmed that all the enrichment cultures exhibiting sulfurous acid gas resistance share a common feature of containing betaine in the cells in an environment having the salt concentration close the growth limit. These findings suggested a further strong relationship between betaine and sulfurous acid gas resistance and revealed that the betaine production mechanism or the intracellular concentration of betaine is deeply involved in the sulfurous acid gas resistance mechanism.

Further, among all the enrichment cultures used in the current series of experiments, the enrichment culture that exhibited sulfurous acid gas resistance with the lowest salt concentration was found in the culture condition category having the sulfurous acid gas concentration of 5 ppm and the salt concentration of 10 wt. %. The algae bodies cultured in this category were recovered to prepare a freeze-dried specimen. The freeze-dried specimen was subjected to a separation/detection method using a high performance liquid chromatography to measure the concentration of betaine in the specimen. As a result, it was confirmed that the specimen contained betaine in an amount of 1 wt. % on a dry weight basis of the algae bodies (cells).

If the sulfurous acid gas concentration of 5 ppm was set as a standard for sulfurous acid gas resistance of the microalgae used in the present invention, it was found that the microalgae could exhibit sulfurous acid gas resistance at the concentration of 5 ppm by containing about 1 wt. % of betaine on a dry weight basis in the cells.

Next, using a *Galdieria partita* NBRC102759 microalgae strain (hereinafter referred to as *Galdieria* known resistant strain) that was known to be resistant to sulfurous acid gas by Japanese Patent No. 3459275, a relationship between sulfurous acid gas resistance (0, 5, 10, and 50 ppm) and the salt concentration was examined under the various culture conditions by following above experiments.

The above relationship was examined by setting the salt concentration of the culture solution of the *Galdieria* known resistant strain at 0, 3, and 5 wt. % to find that as the salt concentration increased, sulfurous acid gas resistance also tended to increase.

This tendency was the same as the case of the enrichment culture BAH11, however, the results showed that the lowest salt concentration that induced sulfurous acid gas resistance was different between the *Galdieria* known resistant strain and the enrichment culture BAH11.

The results are shown in Table 3.

In Table 3, a peak culture concentration of the *Galdieria* known resistant strain is indicated by a numerical value of PCV (packed cell volume: ml/L) in a combination of the salt concentration and the sulfurous acid gas concentration blown. The higher value of PCV indicates the higher peak culture concentration (growth efficiency) of the *Galdieria* known resistant strain.

TABLE 3

Changes of sulfurous acid gas resistance (peak culture concentration) in Galdieria known resistant strain

| | | Salt concentration (wt. %) | | |
|---|---|---|---|---|
| | | 0 | 3 | 5 |
| Sulfurous acid gas concentration (ppm) | 0 | 7.3 | 7.8 | 8.5 |
| | 5 | 4.2 | 8.3 | 7.9 |
| | 10 | 0.0 | 7.3 | 8.3 |
| | 50 | 0.1 | 8.0 | 8.1 |

Values in table represent peak culture concentration: PCV(ml/L)

Next, an intracellular osmotic pressure adjusting substance was examined under the various salt concentration conditions using $^{13}$C-NMR to find that the osmotic pressure adjusting substance contained in the *Galdieria* known resistant strain cells was betaine.

From the present experimental results, sulfurous acid gas resistance of the microalgae *Galdieria* described in Japanese Patent No. 3459275 is thought to be exhibited depending on the betaine content in the *Galdieria* cells. However, to the best of knowledge of the inventors, there is no known document that suggests the above theory based on the present experiment.

The above findings suggested a further strong relationship between the betaine content and sulfurous acid gas resistance and demonstrated that the betaine synthesis ability of the microalgae or the intracellular concentration of betaine was deeply involved in sulfurous acid gas resistance.

Example 2 (Second Embodiment)

Results of a verification test of the second embodiment performed using an exhaust gas containing sulfurous acid gas in an outdoor bench scale were shown below. The present verification test is intended to verify an integrated production process from the recovery of carbon dioxide by the microalgae having sulfurous acid gas resistance to the production of useful organic materials including betaine as an example, and to evaluate a degree of contamination of other microalgae, which occasionally occurs during a conventional extensive culture. In the outdoor culture, the enrichment culture having sulfurous acid gas resistance and the microalgae not having sulfurous acid gas resistance, which could grow faster than the former enrichment culture in the presence of a normal blowing gas without sulfurous acid gas, were mixed together and cultured. Then, the growth of both microalgae was observed in the presence or absence of sulfurous acid gas.

Specific test procedures will be described below.

(a) The aforementioned enrichment culture BAH11 having sulfurous acid gas resistance and an enrichment culture SHN4 not having sulfurous acid gas resistance were algae used in the test. Morphological observation revealed that the enrichment culture BAH11 contained blue-green algae, *Halothece* genus, as a dominant species. The betaine content of the enrichment culture BAH11 increased when the salt concentration of the culture solution became 5 wt. % or more. The growth of the enrichment culture BAH11 was observed until the salt concentration of the culture solution became nearly 30 wt. %, which was almost the saturation concentration of NaCl. Similarly, the growth of the enrichment culture SHN4 was observed until the salt concentration became high, nearly the saturation concentration of salt. Morphological observation revealed that the enrichment culture SHN4 mainly contained green algae, *Dunaliella* genus.

(b) The preliminary cultures of two enrichment cultures described above were performed separately in an aerating culture using a jar fermenter having a volume of 10 L under the irradiation of fluorescent lighting having a photon flux density of 150 $\mu mol \cdot m^{-2} \cdot s^{-1}$. A culture solution was prepared using an aqueous solution mainly containing the MC medium and Daigo's artificial seawater SP (Wako Pure Chemical Industries, Ltd.). Further, the salt concentration of the culture solution was adjusted to about 25 wt % by adding NaCl. Subsequently, the pH of the culture solution was adjusted to pH4 with diluted sulfuric acid and then further adjusted to pH8 by adding sodium carbonate. In the both preliminary cultures of the enrichment cultures, the pH of the culture solution after starting the cultures at a constant thermostatic condition of 35° C. was adjusted using a pH stat in a range of pH6 to 7 by blowing an air containing 0.5 vol. % carbon dioxide.

(c) Subsequently, the enrichment cultures in the preliminary cultures were harvested at a linear phase and transferred to a main culture having a large capacity. Specifically, the microalgae of the both enrichment cultures harvested from the preliminary cultures were mixed and inoculated into the same outdoor incubator of one cubic meter capacity tank, in which a reinforced vinyl chloride bag was supported by a iron fence, at a concentration of 0.1 ml per 1 L of the culture solution (PCV concentration). The culture solution used in the main culture is the same as the preliminary culture. Further, the pH was adjusted by blowing a carbon dioxide enriched air using the same system as in the preliminary culture. Another culture system having the same configuration was prepared to set up two identical culture systems in order to perform a comparison test below.

(d) The following two test specimens were set.
(Test specimen 1): Added test specimen in which 50 ppm sulfurous acid gas was added to pH adjusting gas
(Test specimen 2): Sulfurous acid gas-free test specimen The PCV concentration was used as a growth index of the microalgae and the like in the above cultures. Further, morphological changes of the microalgae in the mixed cultures were examined using an optical/fluorescence microscope.

The experimental results are shown in Table 4.

TABLE 4

Effects on microalgae culture caused by presence or absence of sulfurous acid gas in blowing gas

|  | 1. Initial concentration (ml/L) | 2. Peak concentration (ml/L) | 3. Maximum water temperature (° C.) | Dominant microalgae after culturing |
|---|---|---|---|---|
| Test specimen 1 (with sulfurous acid gas) | 0.2 | 12 | 35 | *Halothece*-like |
| Test specimen 2 (without sulfurous acid gas) | 0.2 | 10 | 36 | *Dunaliella*-like |

As is apparent from the results in Table 4, the growth of microalgae was confirmed in the both test specimens. However, the color tone of the culture solution was different between two test specimens. Specifically, the color tone of the test specimen 2 was a pale green at the initiation of the culture and changed to orange in the late stage of the culture. On the other hand, the color tone of the test specimen 1 was a pale green at the initiation of the culture and changed to blue-green along with culturing time. After completion of the culturing, the cultures were observed with a microscope. In the culture of the test specimen 2, *Dunaliella* genus having orange color was a dominant species and a proportion of *Halothece* genus was less than several percents. On the other hand, in the culture of the test specimen 1, *Halothece* genus became a dominant species and there was no *Dunaliella* genus observed. However, semi-transparent objects, which might be debris of *Dunaliella* genus cells, were observed albeit a very small amount.

When the cultures were examined with a fluorescence microscope, it was observed that chloroplasts in *Dunaliella* genus cells emitted red fluorescence and chloroplasts in *Halothece* genus cells emitted orange fluorescence. In the culture of the test specimen 2, both fluorescences were observed, but in the culture of the test specimen 1, where sulfurous acid gas was blown, cells emitting red fluorescence were not present at all, and the culture was occupied with cells emitting orange fluorescence.

The culture of the test specimen 1 was recovered after completion of the culturing and a specimen was fractionated from the culture for measuring the betaine concentration by a separation/detection method using a high performance liquid chromatography. As a result, it was confirmed that the specimen contained betaine in an amount of 18 wt. % on a dry weight basis of the algae bodies (cells).

On the other hand, the betaine concentration of the culture in the test specimen 2, recovered after completion of the culturing, was only 3 wt. % on a dry weight basis.

Betaine is commonly extracted from sugar beet and supplied to the market. The intracellular content of betaine in the algae bodies cultured in the test specimen 1 was found to be about 90-fold higher in concentration than the betaine content in the sugar beet.

In summary, the microalgae having hydrogen sulfide gas resistance and sulfurous acid gas resistance were cultured in the verification test in an outdoor bench scale to show that carbon dioxide could be recovered from the mixed gas containing sulfurous acid gas and useful organic materials could be further produced. That is, the test could verify an integrated production process from the recovery of carbon dioxide to the production of organic materials.

Further, it was demonstrated that the growth rate of the algae containing betaine in an amount of 1 wt. % or more and having hydrogen sulfide gas resistance and sulfurous acid gas resistance was sufficiently high in the presence of sulfurous acid gas, thus they could overwhelmingly grow over competing undesired microalgae. Thus, it was demonstrated that, according to the present invention, using the algae containing betaine in an amount of 1 wt. % or more made it easy to maintain both the purity and the productivity of biomass obtained from the desired algae at a extremely high level in performing a simple and inexpensive extensive culture, thereby enabling to constitute an integrated production process from the recovery of carbon dioxide to the production of useful organic materials.

The constitutions, combinations thereof, and the like, which are illustrated in the above-described embodiments, are examples, and additions, omissions, substitutions, and other modifications of the constitutions can be made without departing from the scope of the invention.

INDUSTRIAL APPLICABILITY

Regarding industrial production of betaine and the like, the present invention can provide a biological production method capable of efficiently producing betaine throughout the year with a simple step, and such a technique can be applied to meet a large amount of demand for betaine and the like requested by the market.

Further, in an outdoor large-scale culture of microalgae, an exhaust gas containing sulfurous acid gas from a thermal power plant can be directly used as a source of carbon dioxide, while minimizing contamination of other microalgae. As such, the present invention can be widely applied to the implementation of a mass culture and the like that satisfies both the purity and the productivity of biomass.

REFERENCE SIGNS LIST

1: Enrichment culture preparation step
2: Cultivation plan step
3: Main cultivation step (including: step of separating and obtaining osmotic pressure adjusting substance)
4: Betaine
5: Glucosyl glycerol
6: Sodium chloride
11: Mixed gas containing sulfurous acid gas in addition to carbon dioxide (exhaust gas from power plant, etc.)
12: Carbon dioxide gas
13: Sulfurous acid gas
14: Desulfurization apparatus
15: Diluting gas (air, etc.)
16: Culture tank (reaction tank for fixing carbon dioxide)
17: Light source (sun light, etc.)
18: Nutrient salts (including medium components or some organic materials, etc.)
19: Biomass processing step after culturing (recovery/extraction/purification/drying, etc.)
20: Valuable substance (market product)

The invention claimed is:

1. An algae culture method, comprising:
   a) an enrichment culture preparation step for preparing a plurality of enrichment cultures, each including microalgae that contain betaine in an amount of 1 wt. % or more on a dry weight basis and having a different dominant species of microalgal flora, by culturing an environmental specimen or a culture of microalgae grown from the environmental specimen under a photoautotrophic condition and under a plurality of different culture conditions that include at least one of a temperature condition, a pH condition, and a salt concentration condition in which a final salt concentration in the culture is adjusted to 10 wt. % or more and 30 wt. % or less;
   b) a step of selecting an optimum enrichment culture from the plurality of enrichment cultures by its response to an estimated temperature change and pH change caused in a medium during a main cultivation; and
   c) subculturing the optimum enrichment culture selected in step (b) at different temperatures and different pH's, to identify microalgal cultures that grow at the desired temperatures and pH's; wherein the main cultivation step produces a main culture that contains the microalgae containing the betaine in an amount of 1 wt. % or more on a dry weight basis when the main culture is grown photoautotrophically and in a medium having the salt concentration in step (a).

2. The algae culture method according to claim 1, wherein the betaine is separated and obtained from the main culture simultaneously with and/or after the main cultivation step.

3. The algae culture method according to claim 1, wherein, in the main cultivation step, the main culture is performed under the salt concentration condition of 10 wt. % or more and 30 wt. % or less and a temperature condition of 30° C. or higher and lower than 50° C.

4. The algae culture method according to claim 1, wherein, in the enrichment culture preparation step, the environmental specimen is collected from a natural environment which the microalgae inhabit.

5. The algae culture method according to claim 1, wherein the main cultivation step further includes
   a) a second enrichment culture step for selecting, from the plurality of enrichment cultures, a second enrichment culture capable of growing at the temperature of the first enrichment culture and at pH 4 or lower to avoid a decrease in the cell number of the microalgae due to predation by a predatory organism, and
   b) performing the main cultivation step at a pH of 4 of lower.

6. The algae culture method according to claim 5, wherein the main cultivation step is performed throughout a year and the second enrichment culture step is performed at a temperature that depends on the current temperature change.

7. The algae culture method according to claim 1, wherein, in the main cultivation step, the microalgae containing the betaine in an amount of 1 wt. % or more on a dry weight basis are cultured while blowing a mixed gas containing sulfurous acid gas and carbon dioxide to a culture solution of the microalgae.

8. The algae culture method according to claim 7, wherein the microalgae are resistant to hydrogen sulfide gas.

9. The algae culture method according to claim 7, wherein the microalgae are resistant to sulfurous acid gas.

10. The algae culture method according to claim 7, wherein the salt concentration in the culture solution is 3 to 30 wt. %.

11. The algae culture method according to claim 7, wherein the concentration of sulfurous acid gas in the mixed gas is more than 5 ppm.

12. The algae culture method according to claim 7, wherein the mixed gas is generated by burning a sulfur-containing substance.

13. The algae culture method according to claim 7, wherein the microalgae are an enrichment culture obtained by inoculating water or soil collected from the natural environment which the microalgae inhabit into the culture solution and selecting microalgae which succeeded in growing in the culture.

14. A method of producing betaine, comprising:
a) an enrichment culture preparation step for preparing a plurality of enrichment cultures each including microalgae that contain betaine in an amount of 1 wt. % or more on a dry weight basis and having a different dominant species of microalgal flora, by culturing an environmental specimen containing microalgae or a culture of microalgae grown from the environmental specimen under a photoautotrophic condition and under a plurality of different culture conditions that include at least one of a temperature condition, a pH condition, and a salt concentration condition in which a final salt concentration in a culture is adjusted to 10 wt. % or more and 30 wt. % or less;
b) a step of selecting an optimum enrichment culture from the plurality of enrichment cultures by its response responding to an estimated temperature change and pH change caused in a medium during a main cultivation;
c) subculturing the optimum enrichment culture selected in step (b) at different temperatures and different pH's, to identify microalgal cultures that grow at the desired temperatures and pH's, wherein the main cultivation step produces a main culture that contains the microalgae containing the betaine in an amount of 1 wt. % or more on a dry weight basis when the main culture is grown photoautotrophically and in a medium having the salt concentration in step (a); and
d) separating the betaine from the main culture simultaneously with and/or after the main cultivation step, thereby obtaining the betaine.

* * * * *